US008983626B2

(12) United States Patent
Zarembo et al.

(10) Patent No.: US 8,983,626 B2
(45) Date of Patent: Mar. 17, 2015

(54) STIMULATION CUFF AND IMPLANTATION TOOL

(71) Applicant: Cardiac Pacemakers, Inc., St. Paul, MN (US)

(72) Inventors: Paul E. Zarembo, Vadnais Heights, MN (US); Bruce A. Tockman, Scandia, MN (US)

(73) Assignee: Cardiac Pacemarkers, Inc., St. Paul, MN (US)

( * ) Notice: Subject to any disclaimer, the term of this patent is extended or adjusted under 35 U.S.C. 154(b) by 0 days.

(21) Appl. No.: 14/141,702

(22) Filed: Dec. 27, 2013

(65) Prior Publication Data

US 2014/0188202 A1 Jul. 3, 2014

Related U.S. Application Data

(60) Provisional application No. 61/746,800, filed on Dec. 28, 2012.

(51) Int. Cl.
*A61N 1/05* (2006.01)

(52) U.S. Cl.
CPC .................................. *A61N 1/0556* (2013.01)
USPC ....................................................... 607/118

(58) Field of Classification Search
CPC .................................................. A61N 1/0556
USPC ......................................... 606/129; 607/118
See application file for complete search history.

(56) References Cited

U.S. PATENT DOCUMENTS

| 4,177,818 A | 12/1979 | De Pedro |
| 4,573,481 A | 3/1986 | Bullara |
| 4,590,946 A | 5/1986 | Loeb |
| 4,590,949 A | 5/1986 | Pohndorf |
| 4,602,624 A | 7/1986 | Naples et al. |
| 4,628,942 A | 12/1986 | Sweeney et al. |
| 4,740,170 A | 4/1988 | Lee et al. |

(Continued)

FOREIGN PATENT DOCUMENTS

| EP | 0585553 A1 | 6/1993 |
| JP | 2005058456 A | 3/2005 |

(Continued)

OTHER PUBLICATIONS

International Preliminary Examination Report, Chapter II, issued in PCT/US2013/029306, completed Aug. 19, 2014, 16 pages.

(Continued)

*Primary Examiner* — George Evanisko
(74) *Attorney, Agent, or Firm* — Faegre Baker Daniels LLP (57) ABSTRACT

Various embodiments concern wrapping a stimulation cuff around a nerve. The cuff can comprise a main body and at least one electrode. The main body can comprise an inner tab, an outer tab, and an intermediate portion extending between the inner tab and the outer tab, the at least one electrode disposed on the intermediate portion, the main body biased such that the cuff assumes the coiled arrangement. The cuff can be uncoiled by pulling on a first elongate element attached to a first tubular member, the first tubular member encircled within the cuff. The nerve can be engaged with an inner surface of the main body along the intermediate portion while the inner tab is releaseably attached to the first elongate element. The first elongate element can be released to allow the cuff to wrap around the nerve.

15 Claims, 10 Drawing Sheets

(56) References Cited

U.S. PATENT DOCUMENTS

| | | | |
|---|---|---|---|
| 4,920,979 A | 5/1990 | Bullara | |
| 4,940,065 A | 7/1990 | Tanagho et al. | |
| 4,979,511 A | 12/1990 | Terry, Jr. | |
| 5,031,621 A | 7/1991 | Grandjean et al. | |
| 5,095,905 A | 3/1992 | Klepinski | |
| 5,218,089 A | 6/1993 | Mariotti et al. | |
| 5,251,634 A | 10/1993 | Weinberg | |
| 5,259,394 A | 11/1993 | Bens | |
| 5,282,468 A | 2/1994 | Klepinski | |
| 5,324,322 A | 6/1994 | Grill, Jr. et al. | |
| 5,334,438 A | 8/1994 | Saugnac | |
| 5,344,438 A * | 9/1994 | Testerman et al. | 607/118 |
| 5,351,394 A | 10/1994 | Weinberg | |
| 5,358,516 A | 10/1994 | Myers et al. | |
| 5,375,594 A | 12/1994 | Cueva | |
| 5,505,201 A | 4/1996 | Grill, Jr. et al. | |
| 5,531,778 A | 7/1996 | Maschino et al. | |
| 5,674,272 A | 10/1997 | Bush et al. | |
| 5,689,877 A | 11/1997 | Grill et al. | |
| 5,755,766 A | 5/1998 | Chastain et al. | |
| 5,782,892 A | 7/1998 | Castle et al. | |
| 5,871,530 A | 2/1999 | Williams et al. | |
| 5,913,876 A | 6/1999 | Taylor et al. | |
| 5,964,702 A | 10/1999 | Grill et al. | |
| 6,038,479 A | 3/2000 | Werner et al. | |
| 6,051,017 A | 4/2000 | Loeb et al. | |
| 6,093,197 A | 7/2000 | Bakula et al. | |
| 6,174,329 B1 | 1/2001 | Callol et al. | |
| 6,178,349 B1 | 1/2001 | Kieval | |
| 6,249,708 B1 | 6/2001 | Nelson et al. | |
| 6,292,703 B1 | 9/2001 | Meier et al. | |
| 6,296,659 B1 | 10/2001 | Foerster | |
| 6,308,104 B1 | 10/2001 | Taylor et al. | |
| 6,308,105 B1 | 10/2001 | Duysens et al. | |
| 6,381,499 B1 | 4/2002 | Taylor et al. | |
| 6,423,080 B1 | 7/2002 | Gellman et al. | |
| 6,600,956 B2 | 7/2003 | Maschino et al. | |
| 6,725,096 B2 | 4/2004 | Chinn et al. | |
| 7,047,081 B2 | 5/2006 | Kuzma | |
| 7,054,692 B1 | 5/2006 | Whitehurst et al. | |
| 7,160,298 B2 | 1/2007 | Lawes et al. | |
| 7,212,867 B2 | 5/2007 | Van Venrooij et al. | |
| 7,502,650 B2 | 3/2009 | Kieval | |
| 7,536,227 B1 | 5/2009 | Poore et al. | |
| 7,561,923 B2 | 7/2009 | Libbus et al. | |
| 7,711,421 B2 | 5/2010 | Shafer et al. | |
| 7,749,273 B2 | 7/2010 | Cauthen, III et al. | |
| 7,807,925 B2 | 10/2010 | Zarembo | |
| 7,831,311 B2 | 11/2010 | Cross, Jr. et al. | |
| 7,891,085 B1 | 2/2011 | Kuzma et al. | |
| 7,925,352 B2 | 4/2011 | Stack et al. | |
| 7,925,358 B2 | 4/2011 | Beiden et al. | |
| 7,933,662 B2 | 4/2011 | Marshall et al. | |
| 7,957,817 B1 | 6/2011 | Gillespie et al. | |
| 7,974,706 B2 | 7/2011 | Moffitt et al. | |
| 7,996,092 B2 | 8/2011 | Mrva et al. | |
| 8,100,141 B2 | 1/2012 | Slupecki et al. | |
| 8,155,757 B1 | 4/2012 | Neisz et al. | |
| 8,244,372 B1 | 8/2012 | Zhulati et al. | |
| 8,295,948 B2 | 10/2012 | Barker et al. | |
| 8,326,418 B2 | 12/2012 | Sommer et al. | |
| 8,417,343 B2 | 4/2013 | Bolea et al. | |
| 8,452,406 B2 | 5/2013 | Arcot-Krishnamurthy et al. | |
| 8,483,845 B2 | 7/2013 | Sage | |
| 8,548,593 B2 | 10/2013 | Ternes et al. | |
| 8,639,355 B2 | 1/2014 | Soltis | |
| 2002/0116042 A1 | 8/2002 | Boling | |
| 2002/0128700 A1 | 9/2002 | Cross, Jr. | |
| 2003/0040785 A1 | 2/2003 | Maschino et al. | |
| 2003/0236558 A1 | 12/2003 | Whitehurst et al. | |
| 2004/0010303 A1 | 1/2004 | Bolea et al. | |
| 2004/0111139 A1 | 6/2004 | McCreery | |
| 2005/0209655 A1 | 9/2005 | Bradley et al. | |
| 2005/0234512 A1 | 10/2005 | Nakao | |
| 2005/0283246 A1 | 12/2005 | Cauthen, III et al. | |
| 2006/0030919 A1 | 2/2006 | Mrva et al. | |
| 2006/0122675 A1 | 6/2006 | Libbus et al. | |
| 2006/0190042 A1 | 8/2006 | Stone et al. | |
| 2006/0259078 A1 | 11/2006 | Libbus | |
| 2007/0071568 A1 | 3/2007 | Dorstewitz | |
| 2007/0083236 A1 | 4/2007 | Sikora et al. | |
| 2007/0100406 A1 | 5/2007 | Kollatschny et al. | |
| 2007/0118177 A1 | 5/2007 | Libbus et al. | |
| 2007/0142871 A1 | 6/2007 | Libbus et al. | |
| 2007/0173914 A1 | 7/2007 | Kollatschny | |
| 2007/0203556 A1 | 8/2007 | Rutten et al. | |
| 2007/0239243 A1 | 10/2007 | Moffitt et al. | |
| 2007/0255320 A1 | 11/2007 | Inman et al. | |
| 2008/0046058 A1 | 2/2008 | Cross et al. | |
| 2008/0051839 A1 | 2/2008 | Libbus et al. | |
| 2008/0058871 A1 | 3/2008 | Libbus et al. | |
| 2008/0058874 A1 | 3/2008 | Westlund et al. | |
| 2008/0058901 A1 | 3/2008 | Ternes et al. | |
| 2008/0086181 A1 | 4/2008 | Amurthur et al. | |
| 2008/0091255 A1 | 4/2008 | Caparso et al. | |
| 2008/0103407 A1 | 5/2008 | Bolea et al. | |
| 2008/0103545 A1 | 5/2008 | Bolea et al. | |
| 2008/0132987 A1 | 6/2008 | Westlund et al. | |
| 2008/0140092 A1 | 6/2008 | Stone et al. | |
| 2008/0172101 A1 | 7/2008 | Bolea et al. | |
| 2008/0177365 A1 | 7/2008 | Bolea et al. | |
| 2008/0177366 A1 | 7/2008 | Bolea et al. | |
| 2008/0183258 A1 | 7/2008 | Inman | |
| 2008/0195188 A1 | 8/2008 | Libbus et al. | |
| 2008/0234780 A1 | 9/2008 | Smith et al. | |
| 2008/0255613 A1 | 10/2008 | Kaiser et al. | |
| 2009/0048641 A1 | 2/2009 | Libbus | |
| 2009/0210042 A1 | 8/2009 | Kowalczewski | |
| 2009/0259260 A1 | 10/2009 | Bentley et al. | |
| 2009/0275997 A1 | 11/2009 | Faltys et al. | |
| 2009/0276024 A1 | 11/2009 | Bonde et al. | |
| 2009/0318961 A1 | 12/2009 | Stone et al. | |
| 2010/0023088 A1 | 1/2010 | Stack et al. | |
| 2010/0036451 A1 | 2/2010 | Hoffer | |
| 2010/0121405 A1 | 5/2010 | Ternes et al. | |
| 2010/0145221 A1 | 6/2010 | Brunnett et al. | |
| 2010/0168831 A1 | 7/2010 | Korivi et al. | |
| 2010/0211131 A1 | 8/2010 | Williams et al. | |
| 2010/0286553 A1 | 11/2010 | Feler et al. | |
| 2010/0305674 A1 | 12/2010 | Zarembo et al. | |
| 2010/0312320 A1 | 12/2010 | Faltys et al. | |
| 2010/0331938 A1 | 12/2010 | Sommer et al. | |
| 2011/0004281 A1 | 1/2011 | Jones | |
| 2011/0022142 A1 | 1/2011 | Barker et al. | |
| 2011/0040257 A1 | 2/2011 | Behymer et al. | |
| 2011/0060395 A1 | 3/2011 | Cantlon | |
| 2011/0172682 A1 | 7/2011 | Brady et al. | |
| 2011/0172701 A1 | 7/2011 | Wales et al. | |
| 2012/0022617 A1 | 1/2012 | Tockman et al. | |
| 2012/0035691 A1 | 2/2012 | Tockman et al. | |
| 2012/0065702 A1 | 3/2012 | Arcot-Krishnamurthy et al. | |
| 2012/0221087 A1 | 8/2012 | Parnis et al. | |
| 2013/0005169 A1 | 1/2013 | Soltis et al. | |
| 2013/0013045 A1 | 1/2013 | Soltis | |
| 2013/0172973 A1 | 7/2013 | Tockman et al. | |
| 2013/0253615 A1 | 9/2013 | Arcot-Krishnamurthy et al. | |
| 2013/0253624 A1 | 9/2013 | Tockman et al. | |
| 2014/0094888 A1 | 4/2014 | True et al. | |

FOREIGN PATENT DOCUMENTS

| | | |
|---|---|---|
| JP | 2008526299 A | 7/2008 |
| WO | WO9929366 A1 | 6/1999 |
| WO | WO2004052176 A2 | 6/2004 |
| WO | WO2006093685 A1 | 9/2006 |
| WO | WO2007024164 A1 | 1/2007 |
| WO | WO2008088798 A1 | 7/2008 |
| WO | WO2008094349 A1 | 8/2008 |
| WO | WO2009020639 A1 | 2/2009 |
| WO | WO2009025817 A2 | 2/2009 |

(56) References Cited

FOREIGN PATENT DOCUMENTS

| | | |
|---|---|---|
| WO | WO2009100242 A2 | 8/2009 |
| WO | WO2011053766 A1 | 5/2011 |

OTHER PUBLICATIONS

Written Opinion of the International Preliminary Examining Authority issued in PCT/US2013/029306, mailed May 8, 2014, 6 pages.
International Search Report and Written Opinion issued in PCT/US2014/015590, mailed May 28, 2014, 14 pages.
International Search Report and Written Opinion Issued in PCT/US2009/063442, mailed Feb. 1, 2010, 11 pages.
International Search Report and Written Opinion Issued in PCT/US2010/026350, mailed Jun. 2, 2010.
International Search Report and Written Opinion Issued in PCT/US2011/020699, mailed Jul. 26, 2011, 24 pages.
International Search Report and Written Opinion Issued in PCT/US2011/049585, mailed Dec. 19, 2011.
International Search Report and Written Opinion Issued in PCT/US2012/044020, mailed Sep. 11, 2012, 9 pages.
International Search Report and Written Opinion issued in PCT/US2012/044028, mailed Oct. 1, 2012, 9 pages.
International Search Report and Written Opinion issued in PCT/US2012/071812, mailed Sep. 13, 2013, 12 pages.
International Search Report and Written Opinion issued in PCT/US2013/029306, mailed Jul. 18, 2013, 13 pages.
International Search Report and Written Opinion issued in PCT/US2013/062560, mailed Dec. 17, 2014, 13 pages.
International Search Report and Written Opinion issued in PCT/US2013/062608, mailed Dec. 17, 2014, 13 pages.
International Search Report and Written Opinion issued in PCT/US2013/077949, mailed Jun. 20, 2014, 15 pages.
Kirsch, Robert F. et al., "Restoration of Hand and Arm Function by Functional Neuromuscular Stimulation", Period covered: Jun. 1, 2001-Aug. 31, 2006, 71 pages.
Partial International Search Report issued in PCT/US2011/020699, mailed Mar. 24, 2011, 6 pages.

\* cited by examiner

STIMULATION CUFF AND IMPLANTATION TOOL

CROSS-REFERENCE TO RELATED APPLICATION

This application claims priority to U.S. Provisional Application 61/746,800, filed Dec. 28, 2012, which is herein incorporated by reference in its entirety.

TECHNICAL FIELD

The present disclosure generally relates to implantable stimulation devices and more specifically to cuffs and tools for implanting the cuffs around nerves and other targets.

BACKGROUND

Implantable stimulation systems can be used for treating various diseases, such as heart failure. An implantable stimulation system may include a pulse generator electrically coupled with a lead. Various types of leads can be used in the body for routing electrical stimulation to a target. One type of lead is a cuff. A cuff can have a generally annular shape to wrap around a nerve or other target. A cuff can have one or more electrodes on the inside of the cuff for delivering stimulation to, and/or receiving electrical signals from, the target. However, being that the cuff may be sized to wrap around a nerve or other small target, the cuff itself can be small and hard to implant along the target. For example, wrapping a cuff around a nerve can be a difficult maneuver to perform in a surgical environment. Accordingly, there is a need for cuffs that can be efficiently and reliably implanted as well as tools to aid in the implantation procedure.

SUMMARY

Example 1 concerns a cuff stimulation system. The system can include a cuff comprising a main body and at least one electrode, the main body comprising an inner tab, an outer tab, and an intermediate portion extending between the inner tab and the outer tab, the at least one electrode disposed on the intermediate portion, the main body biased to assume a coiled arrangement wherein the inner tab is part of an inner most layer and the outer tab is part of an outer most layer, the cuff configured to be uncoiled from the coiled arrangement. The system can further comprise a tool configured to uncoil the cuff and wrap the cuff around a target. The tool can comprise a first tubular member, the first tubular member encircled by the cuff when the cuff is in the curled arrangement, the first tubular member rotatable as the cuff uncoils. The tool can further comprise a first elongate element attached to first tubular member, the first elongate element configured to pull the first tubular member to uncurl the cuff.

In example 2, the system of example 1, wherein the inner tab is configured to engage the first elongate element as the cuff is uncurled to stop the first tubular member from rolling off of the cuff.

In example 3, the system of example 2, wherein the inner tab comprises one or more projections that engage the first elongate element to stop the first tubular member from rolling off of the cuff.

In example 4, the system of example 2, wherein the inner tab comprises one or more slots that receive the first elongate element to stop the first tubular member from rolling off of the cuff.

In example 5, the system of example 2, wherein the inner tab comprises one or more holes through which the first elongate element extends to attach the first tubular member to the inner tab.

In example 6, the system of any preceding example, wherein the cuff has an inner surface and an outer surface that is opposite the inner surface, the one or more electrodes are disposed on the inner surface, and the first tubular member rolls along the inner surface as the cuff uncoils.

In example 7, the system of any preceding example, wherein the cuff has a first width along the intermediate portion and a second width along the inner tab, and the first width is different than the second width.

In example 8, the system of example 7, wherein the first tubular member has a length that is about equal to the first width and less than the second width.

In example 9, the system of any preceding example, wherein the first elongate element is a string.

In example 10, the system of any of examples 1-8, wherein the first elongate element is rigid wire.

In example 11, the system of any preceding example, wherein the tool further comprises a second tubular member, the second tubular member underneath at least one layer of the main body when the cuff is in the curled arrangement. The tool can further comprise a second elongate element attached to the second tubular member, the second elongate element configured to pull the second tubular member to uncurl the cuff, wherein the cuff is uncurled by pulling the first elongate element and the second elongate element in opposite directions.

In example 12, the system of any preceding example, wherein the first elongate element comprises a handle that allows a user to pull the first elongate element to roll the first tubular member over at least a portion of the main body to unroll the cuff.

In example 13, the system of any preceding example, wherein the main body is formed by a base layer and a bias layer.

In example 14, the system of example 13, wherein the bias layer is tapered proximate one or more edges of the main body.

In example 15, the system of any preceding example, wherein a stiffener strip is provided along an edge of the main body.

Example 16 concerns a cuff comprising at least one electrode and a main body. The main body can comprise an inner tab, an outer tab, and an intermediate portion extending between the inner tab and the outer tab such that the inner tab and the outer tab define opposite ends of the main body, the at least one electrode disposed on the intermediate portion, the main body narrower along the intermediate portion and wider along each of the inner tab and the outer tab, wherein the main body is biased such that the cuff assumes a coiled arrangement and the cuff is configured to be uncoiled from the coiled arrangement to wrap around a target.

In example 17, the system of example 16, wherein the inner tab comprises two corners on opposite sides of the inner tab, the two corners configured to engage a tool to hold the cuff in an uncoiled arrangement.

Example 18 concerns a method of wrapping a cuff around a target, the method comprising locating a cuff in a coiled arrangement proximate the target, the cuff comprising a main body and at least one electrode, the main body comprising an inner tab, an outer tab, and an intermediate portion extending between the inner tab and the outer tab, the at least one electrode disposed on the intermediate portion, the main body biased such that the cuff assumes the coiled arrangement. The method can further include uncoiling the cuff, the cuff uncoiled by pulling on a first elongate element attached to a first tubular member, the first tubular member encircled within the cuff. The method can further include engaging the target with the inner surface of the main body along the intermediate portion while the inner tab is releaseably attached to the first elongate element and then releasing the inner tab from attachment with the first elongate element to allow the cuff to wrap around the target.

In example 19, the method of example 18, wherein uncoiling the cuff further comprises pulling on a second elongate element attached to a second tubular member, the second elongate element attached to the outer tab, the second elongate element and the first elongate element pulled in opposite directions to uncoil the cuff.

In example 20, the method of either of examples 19 or 20, further comprising detaching the first elongate element from the inner tab after the cuff is at least partially wrapped around the target.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

BRIEF DESCRIPTION OF THE DRAWINGS

FIGS. 7-9B illustrate various inner tab and tool configurations.

While the disclosure is amenable to various modifications and alternative forms, specific embodiments have been shown by way of example in the drawings and are described in detail below. The intention, however, is not to limit the disclosure to the particular embodiments described herein. On the contrary, the disclosure is intended to cover all modifications, equivalents, and alternatives falling within the scope of the disclosure as defined by the appended claims.

DETAILED DESCRIPTION

Figure 1:
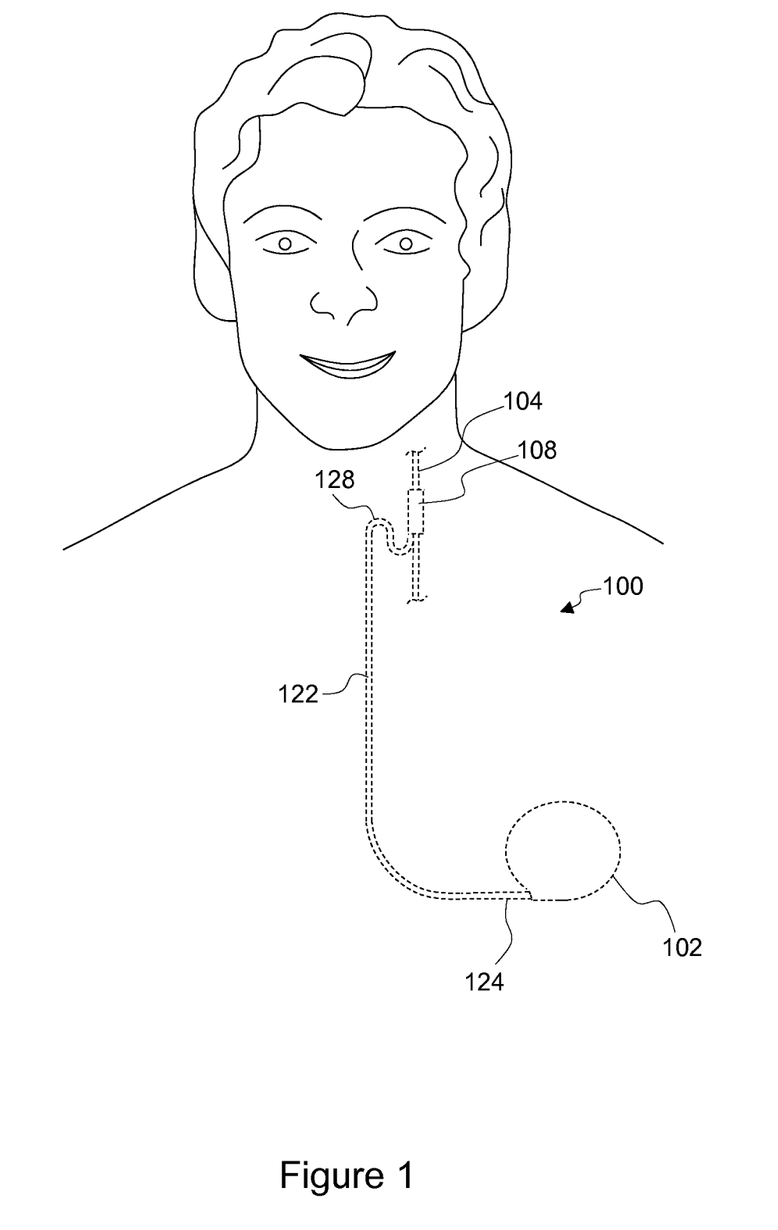
FIG. 1 illustrates an implantable nerve stimulator for treating a patient.

FIG. 1 illustrates a schematic view of an implantable stimulation system 100. The implantable stimulation system 100 can include a pulse generator 102 configured to generate and deliver electrical stimulation. The pulse generator 102 or other implantable medical device can additionally or alternatively be configured to sense signals within the body, such as bioelectrical signals. The pulse generator 102 can be implanted subcutaneously within a patient's chest, neck, abdomen, or other location within the body. The implantable stimulation system 100 can further include a lead body 122. The lead body 122 can comprise a polymer tube having one or more lumens. The lead body 122 can have a proximal portion 124 configured to mechanically and electrically connect with the pulse generator 102. The lead body 122 can have a distal portion 128 configured to mechanically and electrically connect with a cuff 108.

The nerve 104 in FIG. 1 represents a vagus nerve. Stimulating the vagus nerve can have effects on physiological parameters associated with the heart, such as heart rate and blood pressure. Stimulation of the sympathetic and parasympathetic nervous systems via the vagus nerve or other nerve can have therapeutic effects on the brain, the digestive system, the respiratory system, the liver, the kidneys, the intestines, and the bladder, among other systems, organs, and functions. The cuff 108 can include one or more sensors (e.g., electrodes and/or other transducer) for measuring one or more physiological parameters. In some cases, a cuff 108 may not include any sensors. The cuff 108 can be wrapped around a target other than a nerve, such as a blood vessel (e.g., the carotid sheath or internal jugular vein). For example, the cuff 108 can include one or more pressure sensors for measuring blood pressure from the blood vessel. The cuff 108 can be wrapped around multiple targets simultaneously. While the vagus nerve is used as an example target herein, the embodiments of the present disclosure can be applied to any other target or combination of targets. It is noted that the term nerve, as used herein, can refer to a nerve bundle.

Figure 2:
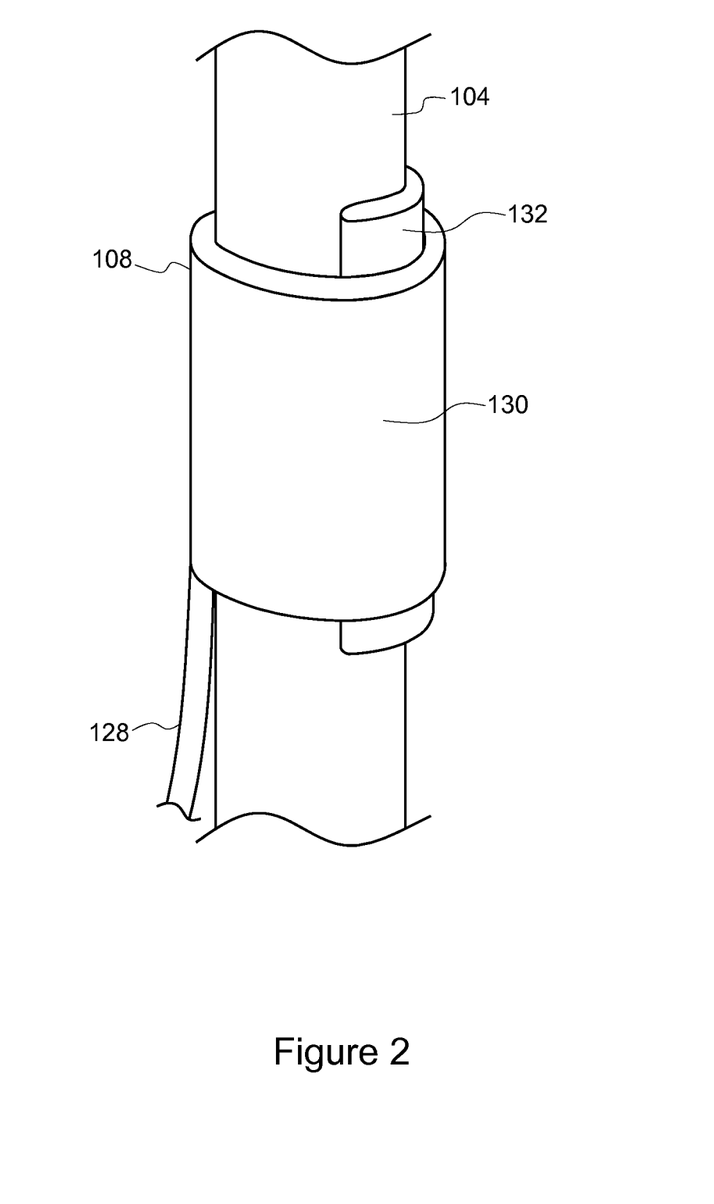
FIG. 2 illustrates a cuff wrapped around a nerve.

FIG. 2 illustrates a perspective view of the cuff 108 wrapped around the nerve 104. The cuff 108 can wrap entirely around the nerve 104. For example, the cuff 108 can overlap itself as shown in FIG. 2. The cuff 108 may wrap around only part of the nerve 104 or other target in some embodiments. The wrapping of the cuff 108 around the nerve 104 can secure one or more electrodes or other sensors in direct contact with the nerve 104. Locating one or more electrodes along the nerve 104 can minimize the electrical energy needed to achieve a therapeutic goal. Also, proximity of the one or more electrodes to the nerve 104 and the use of low energy stimulation can minimize the likelihood of unintentionally stimulating surrounding tissues. Proximity between the one or more electrodes and the nerve 104 can maximize signal reception in sensing applications.

The cuff 108 can be biased such that the cuff 108 assumes a coiled arrangement. Techniques for biasing the cuff 108 are further discussed herein. The bias can allow the cuff 108 to wrap around the nerve 104 and maintain the position indefinitely, thereby securing the cuff 108 to the nerve 104. It is noted that biasing can present challenges during implantation. For example, the cuff 108 may have to be uncoiled before being wrapped around the nerve 104. Various embodiments of the present disclosure concern features and tools to facilitate the uncoiling of the cuff 108 and wrapping the cuff 108 around the nerve 104 or other target.

Figure 3:
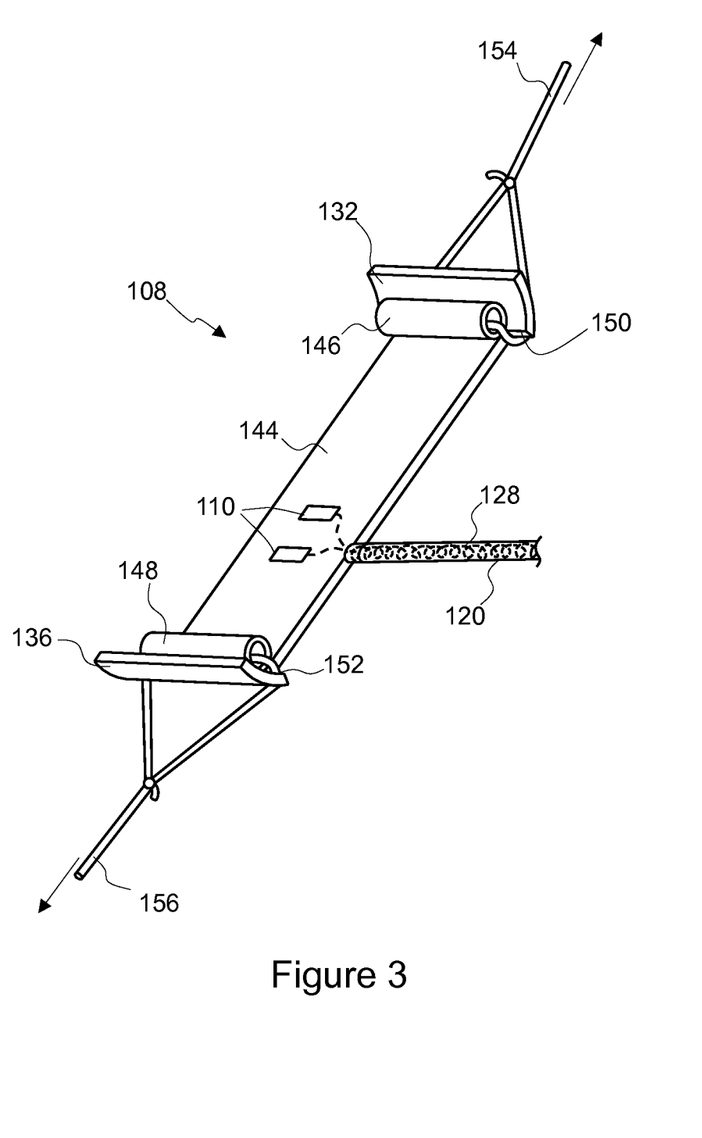
FIG. 3 illustrates a cuff uncoiled with the aid for a tool.

FIG. 3 illustrates a perspective view of the cuff 108 in an uncoiled arrangement. The layout of the cuff 108 is further described in connection with FIG. 4. The cuff 108 can be uncoiled by use of the first elongate element 154 attached to the first tubular member 146, and the second elongate element 156 attached to a second tubular member 148. The first tubular member 146 and the second tubular member 148 can comprise polymer or metal tubes. The first elongate element 154 and the second elongate element 156 can comprise strings (e.g., sutures) or rigid metal wires, for example.

Figure 4:
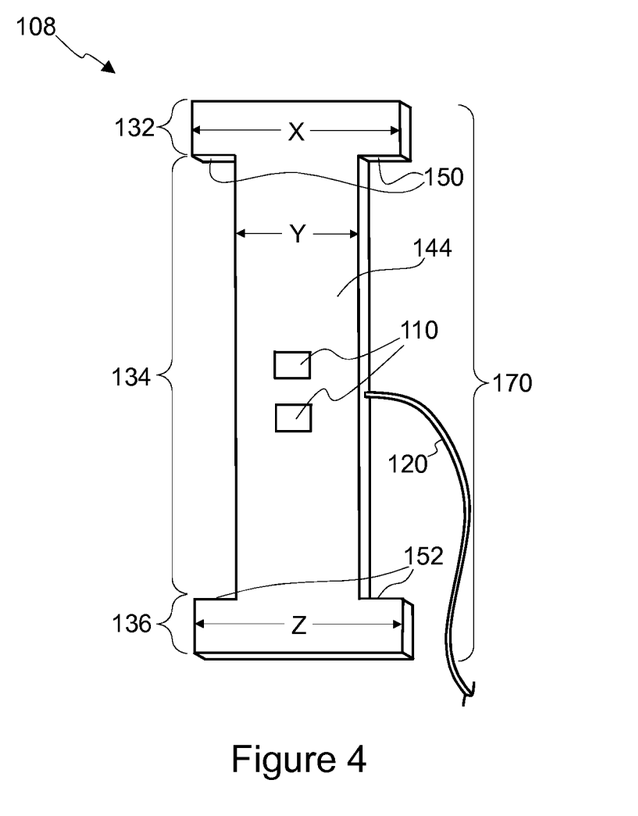
FIG. 4 illustrates a cuff laid flat.

Each of the first elongate element 154 and the second elongate element 156 can be pulled in opposite directions, as shown, to uncoil the cuff 108 and expose the inner surface 144 of the cuff 108. Each of the first tubular member 146 and the second tubular member 148 can roll over the inner surface 144 as the cuff 108 uncoils. The first elongate element 154 can engage corners 150 of the inner tab 132 (both corners 150 are shown in FIG. 4), the engagement stopping the first tubular member 146 from rolling off of the cuff 108. Likewise, the second elongate element 156 can engage corners 152 of the outer tab 136, the engagement stopping the second tubular member 148 from rolling off of the cuff 108. Engagement between the inner tab 132 and the first elongate element 154 can attach the inner tab 132 to the first tubular member 146 and the first elongate element 154. Similarly, engagement of the outer tab 136 with the second elongate element 156 can attach the outer tab 136 to the second tubular member 148 and the second elongate element 156. The cuff 108 can continue to be held open as the cuff 108 is maneuvered and wrapped around the nerve 104.

The length of the first tubular member 146 is about the same as the width of the intermediate portion 134 (shown in FIG. 4). Also, the length of the first tubular member 146 can be less than the width of the inner tab 132. The length of the first tubular member 146 being about the same as the width of the intermediate portion 134 and less than the width of the first tubular member 146 can allow the first elongate element 154, which can extend from both ends of the first tubular member 146, to loop underneath and around the inner tab 132. In this or in other ways, the first tubular member 146 can be dimensioned to align the first elongate element 154 with engagement features (e.g., the corners 150) of the inner tab 132. Likewise, the second tubular member 148 can be dimensioned to align the second elongate element 156 with the corners 152 or other engagement features of the outer tab 136 as described herein.

The cuff 108 can wrap around the nerve 104 such that the inner surface 144 faces toward the nerve 104 while the outer surface 130 (shown in FIG. 2) faces away from the nerve 104. In some embodiments, the inner surface 144 can directly contact the nerve 104. One or more electrodes can be exposed along the inner surface 144 of the cuff 108. Two electrodes 110 are shown in the embodiment of FIG. 3, however this or any other embodiment can have zero, one, three, or more electrodes. The electrodes 110 can be made from any conductive biocompatible material, such as platinum, platinum-iridium, palladium, or stainless steel. The electrodes 110 can comprise one or more of foil, a machined part, a stamped part, electroless deposited metal, a coil, or a cable, among other options. The electrodes 110 can be partially embedded within the material forming the cuff 108. The electrodes 110 can be aligned in various patterns, such as in one or more rows and/or one or more columns. As shown in FIG. 3, one or more conductors 128 can extend within the material of the cuff 108 to electrically connect with respective electrodes 110. The one or more conductors 128 can extend within the lead body 122 to the proximal end 124 to electrically connect with one or more channels of the pulse generator 102. The lead body 122 can be attached to the cuff 108 by adhesive, heat bond, or other connection.

FIG. 4 illustrates an overhead view of the cuff 108 in a fully uncoiled arrangement. It is noted that, in various embodiments, the cuff 108 will not lay flat unrestrained because of the bias of the cuff 108. However, the cuff 108 is shown flat in FIG. 4 to assist in visualization of the sections of the cuff 108. The cuff 108 can comprise a main body 170, the main body 170 having an inner tab 132, an outer tab 136, and an intermediate portion 134 extending between the inner tab 132 and the outer tab 136. Each of the inner tab 132 and the outer tab 136 can be connected to opposite ends of the intermediate portion 134. The inner tab 132 can have a width X, the intermediate portion 134 can have a width Y, and the outer tab 136 can have a width Z. As shown in FIG. 4, the width X and/or the width Z can be greater than the width Y. In some embodiments, the width X and/or the width Z can be less than the width Y. The corners 150 can be formed by the inner tab 132 being wider than the intermediate portion 134. Also, the corners 152 can be formed by the outer tab 136 being wider than the intermediate portion 134. The corners 150, 152 can further include notches to receive the first and the second elongate elements 152, 154. While the inner tab 132 and the outer tab 136 include corners 150, 152 to engage the first elongate element 154 and the second elongate element 156 to hold the cuff 108 in an uncoiled arrangement, other tab features can be provided. For example, the inner tab 132 and/or the outer tab 136 can include holes, cut-outs, projections, notches, or any other structures that is dissimilar from the intermediate portion 134 to catch the first elongate element 154 and the second elongate element 156 to stop the first tubular member 146 and the second tubular member 148 from rolling off the cuff 108.

Figure 5:
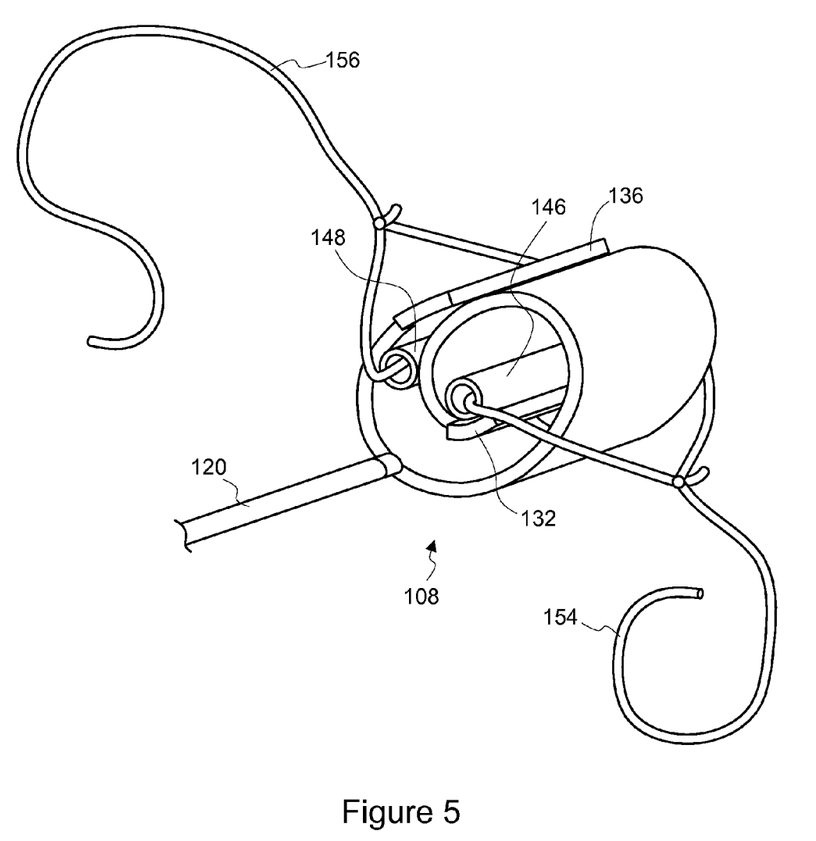
FIG. 5 illustrates a cuff in a coiled arrangement.

FIG. 5 illustrates the cuff 108 in a coiled arrangement. The cuff 108 can be in the coiled arrangement prior to implanting the cuff 108. In some embodiments, the inner tab 132 can be part of an inner most layer of a coiled spiral and the outer tab 136 can be part of an outer most layer of the coiled spiral when the cuff 108 is in the coiled arrangement. As shown, the first tubular member 146 can be encircled within the cuff 108. For example, the first tubular member 146 can extend within the center of a spiral formed by the cuff 108. The second tubular member 148 can extend within the cuff 108 along an outer layer. The first elongate element 154 and the second elongate element 156 are shown in FIG. 5 as flexible strings. The strings can be natural or synthetic sutures, for example. In some other embodiments, the first elongate element 154 and the second elongate element 156 can be wires. The wires can be rigid. Rigid wires can allow the first elongate element 154 and the second elongate element 156 to push as well as pull the first tubular member 146 and the second tubular member 148. While flexible strings may extend out of both ends of the first tubular member 146, a rigid wire may only extend out of one end of the first tubular member 146 (e.g., in an "L" shape). In some embodiments, when a rigid wire is used, a tubular member may not be used. In such cases, the rigid wire may be coated with a lubricious material (e.g., polytetrafluoroethylene) to allow the rigid wire to slide over the inner surface 144 of the cuff 108 in place of the tubular member. The first elongate element 154 and the second elongate element 156 can serve as handles, graspable by hand or by a tool, that are remote from the first tubular member 146 and the second tubular member 148 for uncoiling the cuff 108.

Figure 6A:
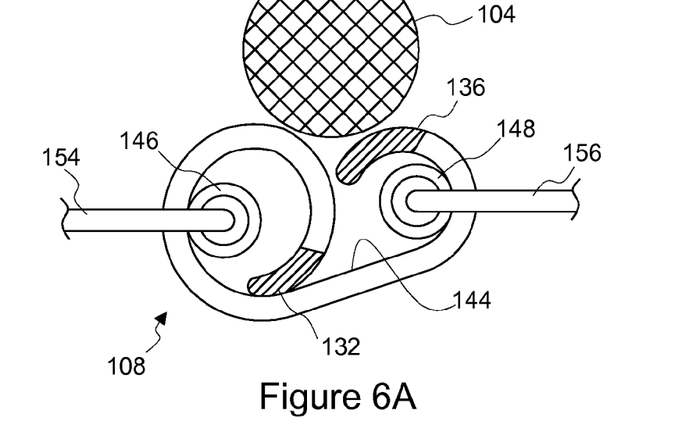
FIGS. 6A-C illustrate a cuff being wrapped around a nerve with a tool.

FIG. 6A is a side view of the cuff 108 with the nerve 104 shown in cross section. The cuff 108 is partially uncoiled in FIG. 6A as the first elongate element 154 and the second elongate element 156 are pulled in opposite directions. As shown, the first tubular member 146 and the second tubular member 148 can roll along the inner surface 144 of the cuff 108. Such rolling action can allow force to be applied to the cuff 108 without scraping or otherwise damaging the cuff 108. Also, the rolling action can allow the location of the application of force to the cuff 108 to be smoothly changed as the cuff 108 uncoils.

Figure 6B:
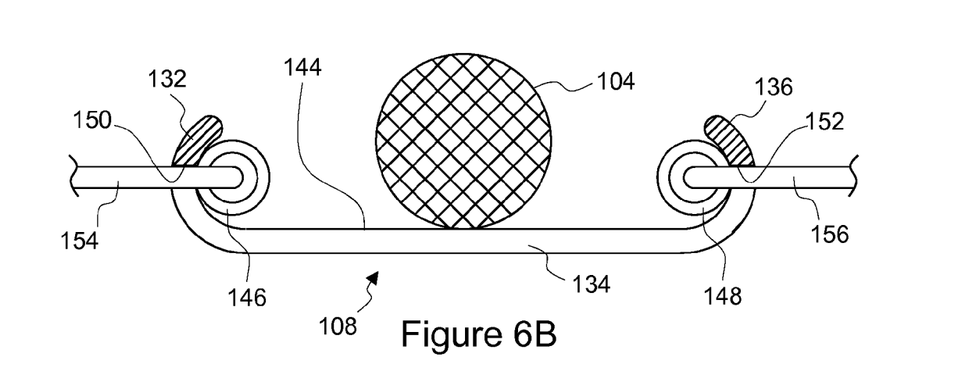

FIG. 6B is continuation of the example of FIG. 6A. The cuff 108 is shown in an uncoiled arrangement in FIG. 6B. In the uncoiled arrangement, the inner surface 144 can be exposed to receive the nerve 104 against the inner surface 144. Furthermore, the inner and outer tabs 132, 136 can be on opposite ends of the cuff 108 in the uncoiled arrangement such that the nerve 104 can be received between the inner and outer tabs 132, 136.

As shown in FIG. 6B, the inner tab 132 can be engaged with the first elongate element 154 and the outer tab 136 can be engaged with the second elongate element 156. Specifically, the first elongate element 154 can be looped around the inner tab 132 and braced against the corner 150. Likewise, the second elongate element 156 can be looped around the outer tab 136 and braced against the corner 152. In these and other ways, the first elongate element 154 can attach to the inner tab 132 and the second elongate element 156 can attach the outer tab 136 to prevent the first tubular member 146 and the second tubular member 148 from rolling off of, and releasing, the cuff 108. The uncoiled arrangement can be maintained as long as the first elongate element 154 and the second elongate element 156 continue to be pulled in opposite directions. The cuff 108 can be wrapped around the nerve 104 while in the uncoiled arrangement. After the cuff 108 is partially or fully wrapped around the nerve 104, one or both of the first elongate element 154 and the second elongate element 156 can be released.

Figure 6C:
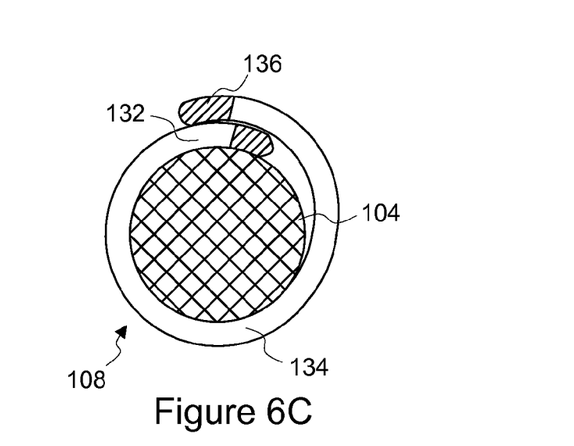

FIG. 6C is continuation of the example of FIG. 6B. The cuff 108 is shown wrapped entirely around the nerve 104 in FIG. 6C. Each of the first tubular member 146 and the second tubular member 148 have been removed from the cuff 108 (e.g., by being slid out from underneath the cuff 108). The first tubular member 146 can be removed by raising the first elongate element 154 over the inner tab 132 such that the first elongate element 154 is no longer looped around the inner tab 132. Additionally or alternatively, the first elongate element 154 and the second elongate element 156 can be configured to be cut by hand tools such as a scalpel, scissors, or a wire cutter. Such cutting can allow the first elongate element 154 to be released from the first tubular member 146. For example, the first elongate element 154 can be removed from the lumen of the first tubular member 146. The first elongate element 154 can be fastened with a knot. The knot may be untied to release the first elongate element 154. The second elongate element 156 and the second tubular member 148 can be removed from the cuff 108 in similar ways. In some cases, both of the first elongate element 154 and the second elongate element 156 can be released at the same time. In some other cases, either of the first elongate element 154 or the second elongate element 156 can be released prior to the release of the other.

In some cases, the first elongate element 154 can be released from attachment with the inner tab 132 by increasing the pulling force on the first elongate element 154. For example, the inner tab 132 can be configured to withstand a particular level of force applied by the first elongate element 154 to maintain the attachment between the inner tab 132 and the first elongate element 154. However, the inner tab 132 can be configured to bend or otherwise deform to release the first elongate element 154 (e.g., the corners 150, 152 can bend) if the force is increased above the particular level of force. In some embodiments, a first level of pulling force can uncurl the cuff 108 and maintain the cuff 108 in the uncoiled arrangement while a second level of pulling force, greater than the first level, can release the first elongate element 154 and allow the cuff 108 to curl around the nerve 104. In some embodiments, the first elongate element 154 or the inner tab 132 can have a weakened spot that is stable at the first level of pulling force but breaks at the second level of pulling force to release the cuff 108. The second elongate element 156 can also be released from attachment with the outer tab 136 by any technique described herein.

Figure 7:
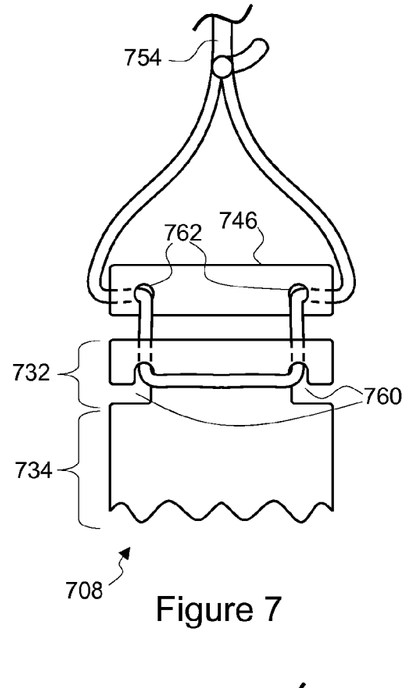
Figure 8:
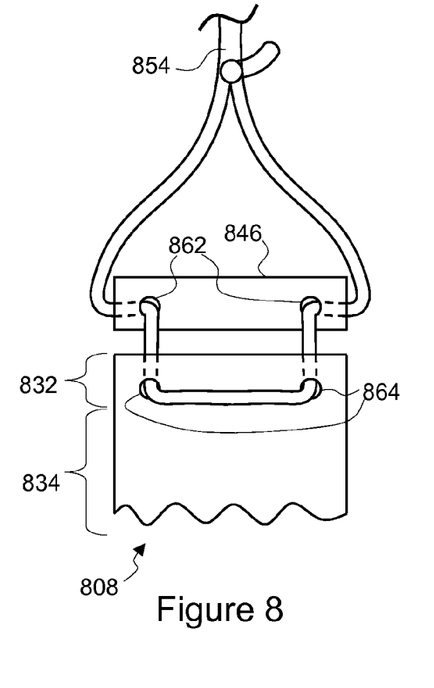
Figure 9A:
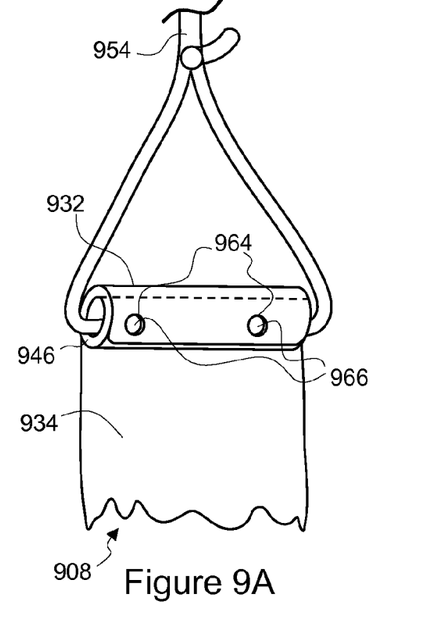
Figure 9B:
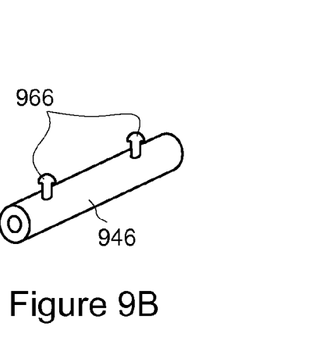

While the inner tab 132 and the outer tab 136 of FIGS. 2-6C can extend laterally beyond the intermediate portion 134 to provide surfaces to engage the first elongate element 154 and the second elongate element 156, various embodiments are not so limited. FIGS. 7-9 illustrate alternative inner tab configurations. In some embodiments, an inner tab can include one or more voids for receiving an elongate element to support attachment between the elongate element and the inner tab. For example, FIG. 7 shows a portion of cuff 708 including an inner tab 732 and an intermediate portion 734. The inner tab 732 can include slots 760. As shown in FIG. 7, the slots 760 can be on opposite sides of the inner tab 732. The slots 760 can receive the elongate element 754.

The elongate element 754 can be threaded through holes 762 within the tubular member 746, the holes 762 provided along a longitudinal exterior surface of the tubular member 746. The holes 762 can be aligned with the slots 762, as shown in FIG. 7. The holes 762 can provide access to a lumen of the tubular member 746. The lumen can be open on each end of the tubular member 746 to allow the elongate element 754 to attach to the tubular member 746. The elongate element 754 can loop around the inner tab 732 by being received within the slots 760 to attach to the inner tab 732.

FIG. 8 shows a portion of a cuff 808 including an intermediate portion 834 and an inner tab 832. The inner tab 832 can be attached to a tubular member 846 and an elongate element 854. The tubular member 846 can include holes 862. The elongate element 854 and the tubular member 846 can be configured similarly to the elongate element 754 and the tubular member 746 of FIG. 7. The inner tab 832 can include holes 864. Although two holes 864 are shown in FIG. 8, a greater or lesser number of holes can alternatively be provided in the inner tab 832. The holes 864 of the inner tab 832 can align with the holes 862 of the tubular member 846 (e.g., the spacing between each set of holes can be similar). The elongate element 854 can be threaded through the holes 864 to attach to the inner tab 832. The elongate element 854 can be cut or untied after the cuff 808 is wrapped around a nerve or other target to allow the elongate element 854 and the tubular element 846 to be removed.

FIG. 9 shows a portion of a cuff 908 including an intermediate portion 934 and an inner tab 932. An elongate element 954 and a tubular member 946 can be attached to the inner tab 932. The tubular member 946 can include pegs 966. The pegs 966 can align with the holes 964 of the inner tab 932 (e.g., the spacing between the pegs 966 and the holes 964 can be similar). The pegs 966 and the holes 964 can be dimensioned such that the pegs 966 can extend through the holes 964 to attach the tubular member 946 and the elongate element 954 to the inner tab 932. The inner tab 932 and part or all of the intermediate portion 934 can be spooled around the tubular member 946 when the cuff 908 is in a coiled arrangement. The elongate element 954 can be pulled to rotate the tubular member 946 and unspool the cuff 908. The inner tab 932 can be lifted off of the pegs 966 to release the inner tab 932 from the elongate element 954 and the tubular member 946.

Various cuff embodiments can have an outer tab that does not include attachment features. For example, the outer tab can have the same width as an intermediate portion and can lack slots, holes, corners, or other features that otherwise facilitate attachment to an elongate element or a tubular member. The outer tab can be on the outer layer of a cuff in a coiled arrangement, and as such can be more easily accessed than an inner tab encircled within the cuff. As such, an outer tab may be grasped (e.g., by tweezers, forceps, or other tool) from the outside of the cuff while a first tubular member, encircled within the coiled cuff, can be pulled by a first elongate element as described herein.

Figure 10:
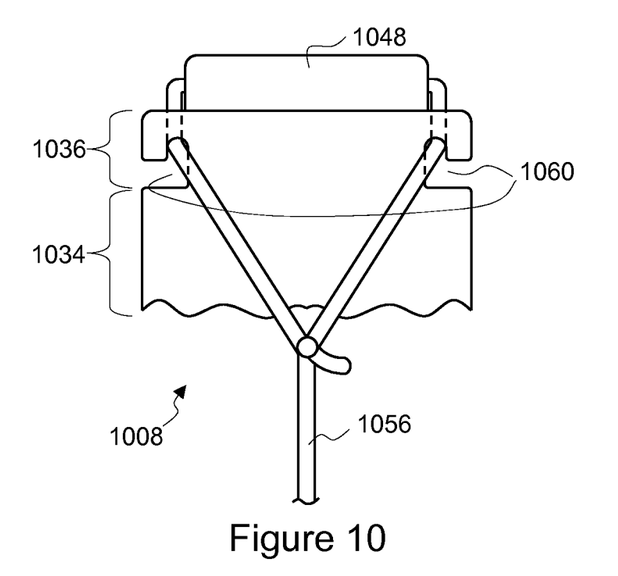
FIGS. 10-11 illustrate various outer tab and tool configurations.
Figure 11:
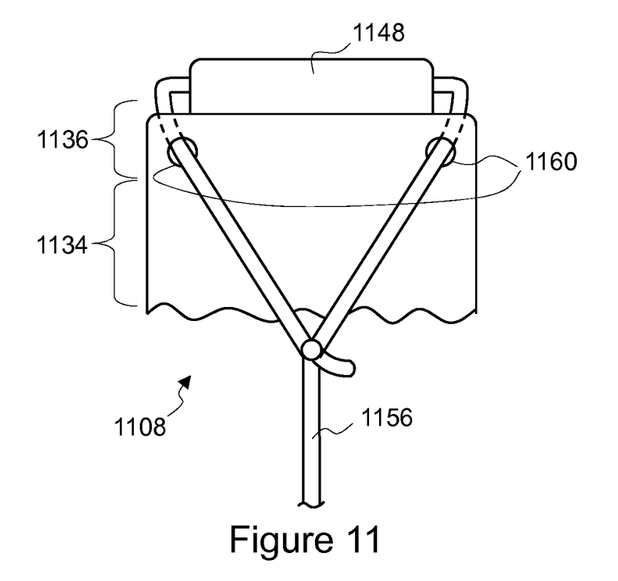

FIGS. 10 and 11 illustrate several outer tab configurations. FIG. 10 shows a portion of a cuff 1008 including an intermediate portion 1034 and an outer tab 1036. The outer tab 1036 can be attached to a tubular member 1048 and an elongate element 1056. As shown, the elongate element 1056 can loop around the outer tab 1036 by being received within the slots 1060. The tubular member 1048 can be removed by cutting, untying, or raising the second elongate element 1056 over the outer tab 1036 such that the second elongate element 1056 is no longer looped around the outer tab 1036.

In various embodiments, the tubular member 1048 may not roll along an inner surface of a cuff 1008 because the outer tab 1036 can be on the outside of the cuff 1008 when in the coiled arrangement. As such, the elongate element 1056 may not need to extend beyond the left and right edges of the cuff 1008. Accordingly, the length of the tubular member 1048 (or other tubular member that attaches with an outer tab) can be less than the width of the outer tab 1036 and the width of the intermediate portion 1034, as shown in FIG. 10.

FIG. 11 shows a portion of a cuff 1108 including an intermediate portion 1134 and an outer tab 1136. The outer tab 1136 can attach to a tubular member 1148, and an elongate element 1156. As shown, the elongate element 1156 can extend through holes 1160 in the outer tab 1136 to loop around the outer tab 1136. The holes 1160 can be aligned with the ends of the tubular member 1148. The tubular member 1148 can be removed by cutting or untying the elongate element 1156. In some cases, the tubular member 1148 and/or the elongate element 1156 can be removed by cutting the outer tab 1136.

Figure 12:
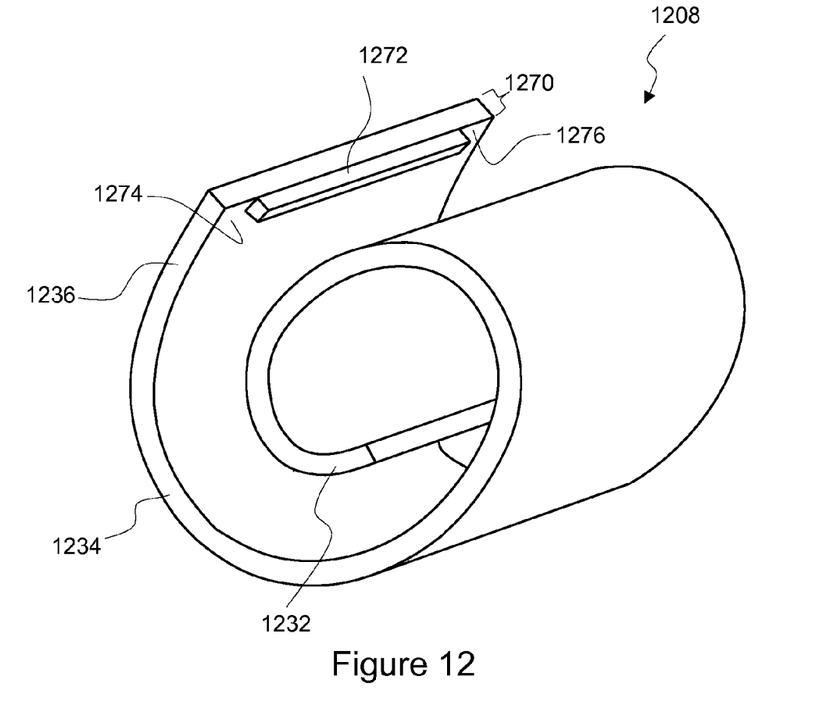
FIGS. 12-14 illustrate the use of a stiffener with a cuff.
Figure 13:
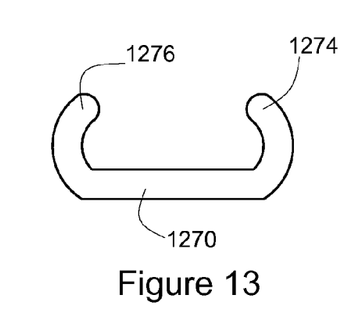
Figure 14:
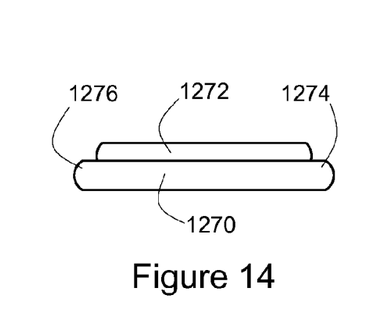

FIG. 12 illustrates a perspective view of a cuff 1208 in a coiled arrangement. The cuff 1208 can include a main body 1270 that defines an inner tab 1232, an outer tab 1236, and an intermediate portion 1234. The main body 1270 can be formed from a single layer or multiple layers of material. One or more layers of the main body 1270 can be pre-stressed to cause the cuff 1208 to assume the coiled arrangement. However, such pre-stressing of the materials of the main body 1270 can cause the edges 1274, 1276 of the cuff 1208 to curl inward as a sub-wrap. Stiffener 1272 (shown in FIGS. 12 and 14) can be provided along the outer tab 1236 to inhibit the edges 1274, 1276 from curling inward. FIG. 13 shows an end view of edges 1274, 1276 curling inward in absence of the stiffener 1272. In contrast to FIG. 13, FIG. 14 shows an end view of edges 1274, 1276 remaining level with the main body 1270 due in part to the presence of the stiffener 1272.

The stiffener 1272 can extend laterally across the cuff 1208. The stiffener 1272 can extend over the entire width of the cuff 1208. Alternatively, the stiffener 1272 may only extend for less than the full width of the cuff 1208. The stiffener 1272 can be provided along either or both of the inner tab 1232 and the outer tab 1236. In some embodiments, the stiffener 1272 may extend along part of the intermediate portion 1234, however the stiffener 1272 may be limited to the inner tab 1232 and/or the outer tab 1236 in various embodiments. The stiffener 1272 can be made from a polymer or metal. The stiffener 1272 can be made from different types of material than the main body 1270. Alternatively, the stiffener 1272 can be made from the same material as the main body 1270 but may not be biased or may be orientated in such a way as to counteract the bias of the main body 1270. The stiffener 1272 may be formed from a stiffer material than the main body 1270. While the stiffener 1272 is illustrated as being disposed on the inner surface of the cuff 1208, the stiffener 1272 can additionally or alternatively be on the outer surface of the cuff 1208 and/or embedded in the main body 1270.

The stiffener 1272 is illustrated in FIG. 12 as a straight strip. In various other embodiments, the stiffener 1272 can be a curved strip (e.g., U-shaped). In some embodiments, the stiffener 1272 can comprise one or more reinforcing strings embedded within or on the main body 1270. In some embodiments, the stiffener 1272 can be a raised portion of the main body 1270 (e.g., an increased thickness in the main body 1270).

Figure 15:
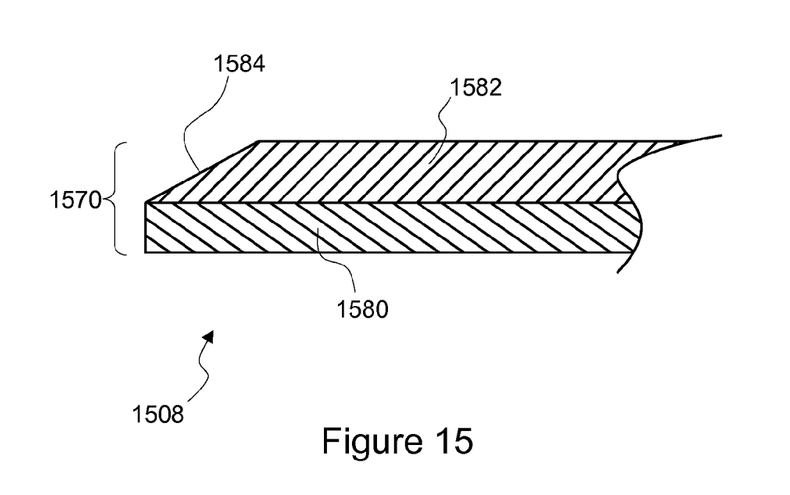
FIGS. 15-16 illustrate cross sectional views of a cuff body.

FIG. 15 illustrates a cross sectional view of the main body 1570 of a portion of a cuff 1508. The portion shown in FIG. 15 can represent any of an inner tab, an outer tab, and/or an intermediate portion as referenced herein. The main body 1570 can be formed by a base layer 1580 and a bias layer 1582. The base layer 1580 and the bias layer 1582 can be formed from similar or different types of material (e.g., one or more polymer materials). In some embodiments, the base layer 1580 can have little or no pre-stress (i.e. no tension within the material when not being deformed) within the material forming the base layer 1580. In some embodiments, the bias layer 1582 can be pre-stressed such that the bias layer 1582 forces the main body 1570 to assume particular shapes, such as a spiral shape.

As mentioned previously, the biasing of a cuff can cause edges, and corners in particular, to curl inward to form a sub-wrap. The main body 1570 of FIG. 15 includes a taper 1584 in the bias layer 1582. The taper 1584 can comprise a thinner bias layer 1582 proximate an edge of the main body 1570 relative to an interior portion of the main body 1570. The taper 1584 can decrease the amount of pre-stressed material proximate an edge of the main body 1570 where sub-wrapping is most likely to occur. Accordingly, the taper 1584 can limit the sub-wrapping of edges of the cuff 1508. In some embodiments, the taper 1584 is provided along an edge of a cuff 1508 to decrease the bias in the cuff 1508 along the edge to limit the degree to which the edge curves. For example, one end of the cuff 1508 can include the taper 1584 such that the end forms a "U" shape, a "C" shape, or a flattened shape, but does not form a spiral shape with the rest of the cuff 1508. The rest of the cuff 1508 may not include the taper 1584 in the bias layer 1582 and may form a spiral shape. The "U" shape or "C" shape can be useful for hooking a nerve or other target with the cuff 1508.

The taper 1584 can be provided along any edge of the cuff 1508. The taper 1584 can also take various shapes. As shown in FIG. 15, the taper 1584 can comprise a linear slope in the bias layer 1582. The taper 1584 can alternatively comprise a curved slope or a series of steps in the bias layer 1582. The bias layer 1582 can be tapered such that the bias layer 1582 does not extend to an edge of the main body 1570.

Figure 16:
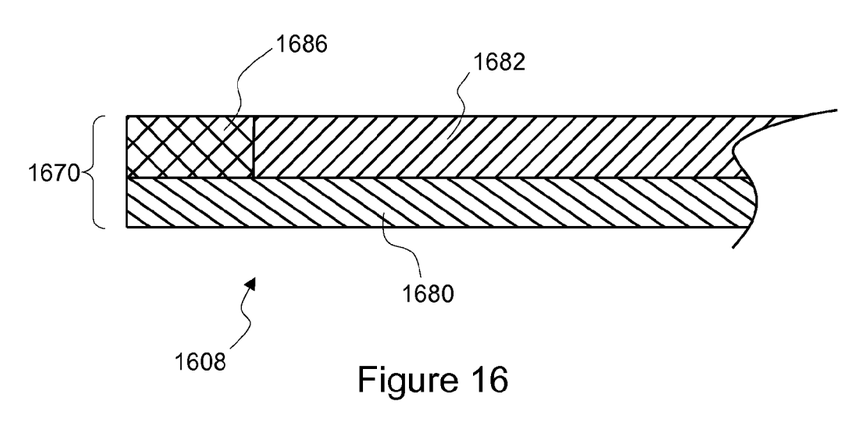

FIG. 16 illustrates a cross sectional view of a main body 1670 of a cuff 1608. The main body 1670 can be formed by a base layer 1680 and a bias layer 1682. The bias layer 1682 may not extend to an edge of the main body 1670. As shown in FIG. 16, a filler layer 1686 can be provided on the edge of the main body 1670 such that the main body 1670 has a uniform surface. The filler layer 1686 can fill in areas where the bias layer 1682 is tapered. The filler layer 1686 can be formed from the same type of material as the base layer 1680. The filler layer 1686 may have little or no pre-stress. In some embodiments, the filler layer 1686 can be pre-stressed in a manner that counteracts the biasing of the bias layer 1682. For example, the filler layer 1686 and the bias layer 1682 can be pre-stressed in different directions.

It is noted that the features of FIGS. 12-16 can be employed in any embodiment described herein (e.g., in the embodiment of FIGS. 1-6C). Likewise, the various options presented herein in separate embodiments may be combinable together into a single embodiment while features presented in a single embodiment can be embodied in separate embodiments.

Moreover, embodiments presented herein as having multiple features can be modified to omit one or more of the features. Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A cuff stimulation system comprising:
   a cuff comprising a main body and at least one electrode, the main body comprising an inner tab, an outer tab, and an intermediate portion extending between the inner tab and the outer tab, the at least one electrode disposed on the intermediate portion, the main body biased to assume a coiled arrangement in which the main body forms an inner layer and an outer layer, wherein the inner tab is part of the inner layer and the outer tab is part of the outer layer of the coiled arrangement, the cuff configured to be uncoiled from the coiled arrangement; and
   a tool configured to uncoil the cuff and wrap the cuff around a target, the tool comprising:
      a first tubular member, the first tubular member encircled by the cuff when the cuff is in the coiled arrangement, the first tubular member rotatable as the cuff uncoils; and
      a first elongate element attached to first tubular member, the first elongate element configured to pull the first tubular member to uncoil the cuff.

2. The system of claim 1, wherein the inner tab is configured to engage the first elongate element as the cuff is uncoiled to stop the first tubular member from rolling off of the cuff.

3. The system of claim 2, wherein the inner tab comprises one or more projections that engage the first elongate element to stop the first tubular member from rolling off of the cuff.

4. The system of claim 2, wherein the inner tab comprises one or more slots that receive the first elongate element to stop the first tubular member from rolling off of the cuff.

5. The system of claim 2, wherein the inner tab comprises one or more holes through which the first elongate element extends to attach the first tubular member to the inner tab.

6. The system of claim 1, wherein the cuff has an inner surface and an outer surface that is opposite the inner surface, the one or more electrodes are disposed on the inner surface, and the first tubular member rolls along the inner surface as the cuff uncoils.

7. The system of claim 1, wherein the cuff has a first width along the intermediate portion and a second width along the inner tab, and the first width is different than the second width.

8. The system of claim 7, wherein the first tubular member has a length that is about equal to the first width and less than the second width.

9. The system of claim 1, wherein the first elongate element is a string.

10. The system of claim 1, wherein the first elongate element is rigid wire.

11. The system of claim 1, wherein the tool further comprises:
    a second tubular member, the second tubular member underneath the outer layer of the main body when the cuff is in the coiled arrangement; and
    a second elongate element attached to the second tubular member, the second elongate element configured to pull the second tubular member to uncoil the cuff, wherein the cuff is uncoiled by pulling the first elongate element and the second elongate element in opposite directions.

12. The system of claim 1, wherein the first elongate element comprises a handle that allows a user to pull the first elongate element to roll the first tubular member over at least a portion of the main body to uncoil the cuff.

13. The system of claim 1, wherein the main body is formed by a base portion and a bias portion.

14. The system of claim 13, wherein the bias layer is tapered proximate one or more edges of the main body.

15. The system of claim 1, further comprising a stiffener strip provided along an edge of the main body.

* * * * *